United States Patent [19]

Kampf

[11] 3,983,183

[45] Sept. 28, 1976

[54] PRODUCTION OF HIGH-VINYL GROUP, LOW-MOLECULAR WEIGHT UNSATURATED HYDROCARBON POLYMERS

[75] Inventor: Wolfgang Kampf, Haltern, Germany

[73] Assignee: Chemische Werke Huls Aktiengesellschaft, Marl, Germany

[22] Filed: Dec. 9, 1974

[21] Appl. No.: 530,549

[30] Foreign Application Priority Data
Dec. 12, 1973  Germany............................ 2361782

[52] U.S. Cl.......................... 260/680 B; 252/429 B; 252/431 P; 526/138; 526/139; 526/335
[51] Int. Cl.²....................... C08F 4/70; C08F 36/06
[58] Field of Search ...................... 252/429 B, 431; 260/94.3, 680 B

[56] References Cited
UNITED STATES PATENTS

| 3,040,016 | 6/1962 | Balas et al. ........................ 260/94.3 |
| 3,066,127 | 11/1962 | Carlson et al. ..................... 260/94.3 |
| 3,428,699 | 2/1969 | Schleimer .......................... 260/94.3 |
| 3,496,247 | 2/1970 | Yuguchi et al. ................... 260/680 B |
| 3,502,637 | 3/1970 | Marullo et al. .................... 260/94.3 |
| 3,522,332 | 7/1970 | Ichikawa et al. ................... 260/94.3 |
| 3,535,303 | 10/1970 | Ichikawa et al. .................. 260/94.3 |
| 3,647,901 | 3/1972 | Sarafidis.......................... 260/680 B |

FOREIGN PATENTS OR APPLICATIONS 1,002,721   8/1965   United Kingdom............ 260/680 B

*Primary Examiner*—Edward J. Smith
*Attorney, Agent, or Firm*—Millen, Raptes & White

[57] ABSTRACT

Low molecular weight polybutadiene, polyisoprene and other hydrocarbon polymers having a high vinyl and a low 1,4-trans-double bond content, which are useful in varnishes and impregnating compositions, are produced employing as catalyst system (a) a cobalt compound; (b) a halogen-containing organoaluminum compound; and (c) an organic phosphite of the formula $PR_1, R_2, R_3$ wherein $R_1$, $R_2$ and $R_3$ are alkoxy, alkenyloxy or monocyclic aryloxy; and optionally (d) an H-acidic compound, e.g., water.

10 Claims, No Drawings

PRODUCTION OF HIGH-VINYL GROUP, LOW-MOLECULAR WEIGHT UNSATURATED HYDROCARBON POLYMERS

BACKGROUND OF THE INVENTION

This invention relates to a process for the production of low molecular weight unsaturated hydrocarbon polymers having an increased proportion of vinyl groups or substituted vinyl groups, respectively.

Several processes have been known for the production of low-molecular weight polybutadienes with a high (>95%) 1,4-content and molecular weights of 500 to 50,000 (German Patents 1,186,631; 1,241,119; and 1,292,853). The products obtained according to this prior-art process are, however, not suitable for all purposes, due to their high 1,4-content. There is a real need for products having an increased proportion of vinyl groups.

It is known from German Published Application DAS 1,770,545 to produce 1,2-polybutadiene having a high percentage of vinyl configuration, by polymerizing butadiene in a halogenated hydrocarbon as the solvent with a catalyst containing as the essential component organic phosphines of the general formula PR'R''R''', wherein R' and R'' are alkyl groups and R''' is an alkyl or aryl group. However, this process is burdened with deficiencies. On the one hand, the halogenated hydrocarbons, which represent the only solvent usable in this method, are very toxic. On the other hand, the phosphines are very expensive and moreover make it possible only with difficulty to produce polymers having molecular weights in the range of interest in varnish technology, viz., below 5,000.

It is an object of this invention to overcome the above-described disadvantages.

SUMMARY OF THE INVENTION

According to this invention, low-molecular weight unsaturated hydrocarbon polymers having an increased proportion of vinyl groups or substituted vinyl groups, respectively, can be produced in a simple and economical manner by the polymerization of conjugated dienes, optionally in the presence of a solvent, employing as the catalyst system:

a. a cobalt compound,
b. a halogen-containing organoaluminum compound, and
c. an organic phosphorus compound, wherein catalyst component (c) is one or more organic phosphorus compounds of the general formula

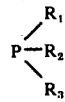

wherein $R_1$, $R_2$ and $R_3$ are alike or different and are $OR_4$, $OR_5$ or $OR_6$ groups wherein $R_4$, $R_5$ and $R_6$ each are alkyl, alkenyl, or monocyclic aryl, i.e., phosphites, and optionally wherein the catalyst system contains as a further catalyst component d. an H-acidic compound.

The thus-produced low molecular weight unsaturated hydrocarbon polymers, especially the polybutadienes, are valuable basic materials, particularly in the varnish and impregnating field, where the properties of the coating agents and/or coatings produced thereby are, as is known, greatly influenced by the distribution of the double bonds in the polymer and the molecular weight thereof.

DETAILED DISCUSSION

In the process of this invention, preferably produced are low-molecular weight polybutadienes having a vinyl group proportion of up to 70%, preferably 10–60%, and polyisoprenes having a proportion of isopropenyl groups of up to 50%, preferably 10–45%, both with a low content of 1,4-transdouble bonds. However, other conjugated dienes can likewise be polymerized in accordance with this process, such as, for example, 1,3-pentadiene, 1,3-hexadiene, 1,3-heptadiene, 1,3-octadiene, 1,3,6-n-octatriene, 1,3,7-n-octatriene, 4-methyl-1,3-pentadiene, 3-methyl-1,3-pentadiene, 3-methyl-1,3-hexadiene, 4-methyl-1,3-hexadiene, 3,7-dimethyl-1,3-octadiene and 5-methyl-1,3,6-heptatriene.

In this process, organic phosphorus compounds of the above general formula are utilized as component (c) of the catalyst system. Accordingly, suitable compounds are phosphites with alkyl, alkenyl, or monocyclic aryl groups. Preferred alkyl groups are straight-chain, branched or cyclic alkyl groups of 1–8 carbon atoms, e.g., methyl, ethyl, propyl, isopropyl, butyl, isobutyl, hexyl, octyl and cyclohexyl. Preferred alkenyl groups are those of up to 6 carbon atoms, e.g., vinyl, allyl and crotyl. Preferred monocyclic aryl groups are e.g., phenyl, tolyl and benzyl.

Examples of phosphites to be utilized are trimethyl, triethyl, tripropyl, tributyl, tricyclohexyl, triallyl, triphenyl, diphenylethyl, diphenylallyl, diphenylbutyl, diethylphenyl and dibutylphenyl phosphite.

Preferred phosphites are those wherein at least two of the groups are the same and especially phosphites wherein at least two of the groups are phenoxy, allyloxy or ethoxy. Triphenyl-phosphite is preferred.

Optionally, the catalyst system contains an H-acidic compound, such as, for example, water, alcohol or an organic acid, i.e., a Bronsted acid. Water is preferred.

The other components of the catalyst system employed in the process of the present invention are (a) a cobalt compound and (b) a halogen-containing organoaluminum compound.

Examples of suitable cobalt compounds are salts of inorganic or organic acids, as well as complex compounds of cobalt, e.g., cobalt chloride, cobalt bromide, cobalt iodide, cobalt sulfate, cobalt sulfide, cobalt nitrate, cobalt carbonate, cobalt phosphate, cobalt cyanate, cobalt cyanide, cobalt hydroxide, cobalt acetate, cobalt oxalate, cobalt valerate, cobalt octoate, cobalt naphthenate, cobalt stearate, cobalt bisacetylacetonate, cobalt bisacetoacetate and dicyclopentadienylcobalt. Examples of other equivalent cobalt compounds will be apparent to those skilled in the art. Preferably, cobalt compounds which are soluble in organic solvents are utilized, for example, cobalt octoate, cobalt acetylacetonate and mixtures thereof.

Examples of preferred halogen-containing organoaluminum compounds are dialkyl aluminum halides, preferably chloride or bromide, e.g., dimethylaluminum chloride, diethylaluminum chloride and diisobutylaluminum chloride, and other dialkylaluminiumhalides of 1–6 carbon atoms in each alkyl group.

The cobalt compound is utilized in catalytic amounts, e.g., 0.001 to 1 millimole, preferably 0.01 to 0.5 millimole, per mole of monomer to be polymerized.

The mixture proportions of the catalyst components can be selected arbitrarily in correspondence with the types of components, the polymerization conditions, and the properties of the polymer to be produced. However, the molar ratio of cobalt to the aluminum in (b) in the catalyst system is 1:1 to 1:2,000, preferably 1:10 to 1:100.

The proportion of the organic phosphorus compound in the catalyst system generally is in the range from 0.1 to 50 moles, preferably 0.3 to 10 moles, per mole of the cobalt compound.

Finally, the molar ratio of the optional H-acidic compound to the aluminum in (b) can be up to 1.5 : 1.

A particular advantage of the catalyst system of this process is that no aging treatment is required prior to its use.

The process of this invention can be carried out continuously or batchwise by contacting the conjugated dienes in contact with the above-described catalyst in a hydrocarbon solvent or a halogenated hydrocarbon solvent, as well as in a bulk process.

Suitable solvents are those basically known in the polymerization with the aid of Ziegler-Natta catalysts. The most important representatives of the group of aliphatic, alicyclic, aromatic and halogenated hydrocarbons are pentane, hexane, heptane, n- and isooctane, isononane (hydrogenated trimer propene), n-decane, isododecane (hydrogenated tetramer propene), cyclopentane, cyclohexane, methylcyclopentane, methylcyclohexane, ethylcyclohexane, isopropylcyclohexane, cyclooctane, decahydronaphthalene, hydrogenated terpenes, such as pinane and camphane, cyclohexane and the substitution products thereof, benzene, toluene, o-, m- and p-xylene, ethylbenzene, o-, m- and p-diethylbenzene, n-propylbenzene, isopropylbenzene and other mono- to polyalkyl benzenes, tetrahydronaphthalene, methylene chloride, chloroform, carbon tetrachloride, 1,2-dichloroethylene, trichloroethylene, tetrachloroethylene, chlorobenzene, o-dichlorobenzene, trichlorobenzene (mixtures of isomers), bromobenzene, fluorobenzene, 1,2-dichloroethane.

However, in view of the polymerization activity, an aromatic hydrocarbon, e.g., benzene, is preferred as the solvent.

The process of this invention is generally conducted at temperatures of −20° to +100° C., preferably 0° to 80° C.

There is no limitation with respect to pressure employed during the polymerization step, as long as it is sufficient to maintain the reaction mixture, especially the monomer to be polymerized, in the liquid phase.

As mentioned above, the hydrocarbon polymers produced according to the process of this invention are characterized by an increased proportion of vinyl or substituted vinyl groups. Thus, e.g., polybutadienes are obtained with a vinyl group content of up to 70%, preferably 10–60%, and polyisoprenes are produced with a content of isoprenyl groups of up to 50%, preferably 10–45%, with a respectively low content of 1,4-trans-double bonds. The proportion of the vinyl or substituted vinyl groups can be controlled by the concentration of the organic phosphorus compound and/or the molar ratio of phosphorus compound to cobalt compound, i.e., with increasing P-concentration the percentage of vinyl groups increases and the molecular weight decreases.

The products obtained according to the process of this invention, primarily the thus-obtained polybutadienes, exhibit generally the following distribution of double bonds:

| | |
|---|---|
| vinyl double bonds | 10 – 70% |
| 1,4-cis-double bonds | 30 – 90% |
| 1,4-trans-double bonds | 0 – 10% |

Besides, they are characterized by a relatively narrow molecular weight distribution (U between 1 and 1.5).

The novel products are suitable for many technical purposes, inter alia as plasticizers for rubbers and for the preparation of air-drying and oven-drying coatings.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the following examples, the reduced specific viscosity (RSV) was determined in toluene at 25° C. The distribution of the double bonds of the polymers was determined by infrared absorption spectra.

EXAMPLE 1

1,675 ml. of benzene, 0.75 millimole of cobalt octoate in the form of a benzenic solution, 0.2 ml. of water (11.1 millimoles), and varying amounts of a benzenic triphenylphosphite solution were introduced at 5° C. in the above-mentioned sequence into a steel autoclave having a capacity of 5 liters. Thereafter, 250 g. of 1,3-butadiene was charged into the vessel. The autoclave was sealed and heated to 25° C. At this temperature, 20 millimoles of diethylaluminum chloride was added. The reactor was heated to 50° C. The polymerization was conducted for a period of 5 hours under agitation.

At the end of the polymerization time, the solution was discharged and mixed with isopropanol and 1% phenyl-β-naphthylamine as the stabilizer. The reaction was thus interrupted. The green solution was then concentrated by evaporation under vacuum.

The results are set forth in Table I.

TABLE I

| Experiment No. | P:Co Molar Ratio | Conversion (%) | RSV (dl/g) | Gel (%) | Microstructure (%) | |
|---|---|---|---|---|---|---|
| | | | | | cis-1,4 | Vinyl |
| 1 | 0.3 | 79.3 | 1.70 | 2 | 86 | 10 |
| 2 | 0.4 | 87.5 | 1.09 | 3 | 81 | 16 |
| 3 | 0.5 | 90.4 | 0.63 | < 2 | 73 | 24 |
| 4 | 0.75 | 87.2 | 0.43 | < 2 | 67 | 28 |
| 5 | 1 | 85.2 | 0.19 | < 2 | 51 | 45 |
| 6 | 1.5 | 88.8 | 0.16 | < 2 | 43 | 54 |
| 7 | 2 | 82.8 | 0.10 | < 2 | 41 | 55 |
| 8 | 5 | 43.2 | 0.06 | < 2 | 41 | 55 |
| Comparative Exp. A | 0 | 89.3 | 2.2 | <2 | 96 | 2 |

EXAMPLE 2

The process as described in Example 1 was repeated, with the modification that, with a constant P : Co ratio of 2 : 1, the quantity of various H-acidic compounds was varied. The results are set forth in Table II.

TABLE II

| Experiment No. | $H_2O$ (mmol) | Conversion (%) | RSV (dl/g) | Gel (%) | Microstructure (%) cis-1,4 | Vinyl |
|---|---|---|---|---|---|---|
| 9 | 0 | 40.0 | 0.06 | <2 | 50 | 44 |
| 10 | 5.55 | 32 | 0.06 | <2 | 46 | 46 |
| 11 | 11.11 | 67.2 | 0.16 | <2 | 40 | 57 |
| 12 | 16.65 | 82.8 | 0.18 | <2 | 41 | 55 |
| 13 | 22.22 | 28 | 0.82 | 2 | 70 | 26 |
| | Iso-propanol (mmol) | | | | | |
| 14 | 2.78 | 43.0 | 0.07 | 2 | 49 | 45* |
| 15 | 5.55 | 31.0 | 0.06 | 2 | 46 | 48 |
| 16 | 11.11 | 19.2 | 0.06 | 5 | 43 | 49 |
| | Trifluoroacetic Acid (mmol) | | | | | |
| 17 | 1.39 | 39.6 | 0.08 | <2 | 49 | 45 |
| 18 | 2.78 | 38.9 | 0.06 | <2 | 49 | 44 |
| 19 | 11.11 | 17.6 | 0.07 | 5 | 49 | 38 |

*The molecular weight of the polymer, determined by vapor pressure osmosis, was $Mn = 1,080$.

EXAMPLE 3

The same mode of operation as decribed in Example 1 was utilized. The cobalt octoate, however, was replaced by other cobalt salts. The results are shown in Table III.

TABLE III

| Experiment No. | $CoCl_2$ (mmol) | P:Co Molar Ratio | Conversion (%) | RSV (dl/g) | Gel (%) | Microstructure (%) cis-1,4 | Vinyl |
|---|---|---|---|---|---|---|---|
| 20 | 0.75 | 0.5 | 44.4 | 0.09 | 2 | 50 | 6 |
| 21 | 0.75 | 2 | 67.2 | 0.11 | <2 | 65 | 20 |
| | Co Acetylacetonate (mmol) | | | | | | |
| 22 | 0.75 | 0.5 | 77.8 | 0.33 | <2 | 79 | 16 |
| 23 | 0.75 | 1 | 49.4 | 0.39 | 2 | 68 | 29 |
| 24 | 0.75 | 2 | 46.1 | 0.12 | <2 | 60 | 34 |
| 25 | 0.75 | 3 | 13.0 | 0.09 | 5 | 45 | 41 |

EXAMPLE 4

The process as set forth in Example 1 was repeated, with the modification that the cobalt salt concentration and the P : Co molar ratio were varied. The results are shown in Table IV.

TABLE IV

| Experiment No. | Co (mmol) | P:Co Molar Ratio | Conversion (%) | RSV (dl/g) | Gel (%) | Microstructure (%) cis-1,4 | Vinyl |
|---|---|---|---|---|---|---|---|
| 26 | 0.1 | 2 | 44.3 | 1.7 | 2 | 89 | 9 |
| 27 | 0.2 | 2 | 65.4 | 0.56 | <2 | 82 | 14 |
| 28 | 0.3 | 2 | 57.9 | 0.27 | 2 | 74 | 22 |
| 29 | 0.5 | 2 | 48.3 | 0.10 | <2 | 51 | 44 |
| 30 | 0.5 | 0.5 | 83.2 | 0.55 | <2 | 82 | 12 |
| 31 | 0.75 | 2 | 75.6 | 0.09 | <2 | 43 | 53 |
| 32 | 1.0 | 2 | 80.0 | 0.07 | <2 | 44 | 51 |
| 33 | 1.0 | 1 | 68.8 | 0.13 | 2 | 48 | 46 |
| 34 | 1.0 | 0.5 | 81.4 | 0.35 | 2 | 80 | 12 |
| 35 | 1.5 | 2 | 70.4 | 0.05 | 2 | 42 | 52 |
| 36 | 1.5 | 0.5 | 92.3 | 0.24 | <2 | 62 | 23 |
| 37 | 2.0 | 2 | 80.8 | 0.03 | <2 | 38 | 57 |

EXAMPLE 5

The process as set forth in Example 1 was repeated, but using higher monomer concentrations. The results are set forth in Table V.

TABLE V

| Experiment No. | Benzene (ml) | Butadiene (mol) | Co Octoate (mmol) | $H_2O$ (mmol) | $Et_2AlCl$ (mmol) | P:Co Molar Ratio | Conversion (%) | RSV (dl/g) | Gel (%) | Microstructure (%) cis-1,4 | Vinyl |
|---|---|---|---|---|---|---|---|---|---|---|---|
| 38 | 1290 | 9.26 | 0.75 | 11.1 | 20 | 2 | 47.8 | 0.08 | <2 | 43 | 53 |
| 39 | 1290 | 9.26 | 1.5 | 22.2 | 40 | 2 | 50.4 | 0.16 | <2 | 38 | 60 |
| 40 | 854 | 13.90 | 2.25 | 33.3 | 60 | 2 | 36.1 | 0.11 | 2 | 42 | 52 |
| 41 | 427 | 20.83 | 3.38 | 50.0 | 70 | 2 | 32.6 | 0.07 | 2 | 40 | 54 |

TABLE V-continued

| Experiment No. | Benzene (ml) | Butadiene (mol) | Co Octoate (mmol) | H₂O (mmol) | Et₂AlCl (mmol) | P:Co Molar Ratio | Conversion (%) | RSV (dl/g) | Gel (%) | Microstructure (%) cis-1,4 | Vinyl |
|---|---|---|---|---|---|---|---|---|---|---|---|
| 42 | 0 | 27.60 | 4.5 | 66.6 | 70 | 2 | 37.5 | 0.05 | < 2 | 38 | 57 |

EXAMPLE 6

The mode of operation of Example 1 was repeated, with the modification that other solvents were used in place of benzene. The results for hexane, cyclohexane, and methylene chloride are compiled in Table VI.

TABLE VI

| Experiment No. | Hexane (ml) | P:Co Molar Ratio | Conversion (%) | RSV (dl/g) | Gel (%) | Microstructure (%) cis-1,4 | Vinyl |
|---|---|---|---|---|---|---|---|
| 43 | 1675 | 2 | 65.8 | 0.13 | 2 | 64 | 23 |
| 44 | 1675 | 1 | 40.3 | 0.14 | 2 | 52 | 35 |
| 45 | 1675 | 0.5 | 69.5 | 0.21 | < 2 | 73 | 17 |
|    | Cyclohexane (ml) |  |  |  |  |  |  |
| 46 | 1675 | 5 | 12.0 | 0.08 | 3 | 33 | 57 |
| 47 | 1675 | 2 | 23.3 | 0.07 | 2 | 37 | 56 |
| 48 | 1675 | 1 | 30.0 | 0.14 | < 2 | 60 | 28 |
| 49 | 1675 | 0.5 | 36.4 | 0.31 | 2 | 74 | 20 |
|    | CH₂Cl₂ (ml) |  |  |  |  |  |  |
| 50 | 1675 | 2 | 40.5 | 0.13 | 2 | 64 | 34 |
| 51 | 1675 | 1 | 37.3 | 0.31 | 2 | 57 | 40 |
| 52 | 1675 | 0.5 | 81.4 | 0.60 | 2 | 66 | 31 |

EXAMPLE 7

Example 1 was repeated, but with the use of different organoaluminum compounds. Table VII contains the results.

TABLE VII

| Experiment No. | Al₂Cl₃Et₃ (mmol) | P:Co Molar Ratio | Conversion (%) | RSV (dl/g) | Gel (%) | Microstructure (%) cis-1,4 | Vinyl |
|---|---|---|---|---|---|---|---|
| 53 | 20 | 2 | 12.2 | 0.06 | 7 | 54 | 21 |
| 54 | 35 | 2 | 68.6 | 1.6 | 28 | 77 | 8 |
|    | AlEtCl₂ (mmol) |  |  |  |  |  |  |
| 55 | 30 | 5 | 62.0 | 0.73 | 22 | 83 | 8 |
| 56 | 40 | 5 | 66.0 | 0.06 | < 2 | 20 | 6 |
| 57 | 40 | 1 | 99.5 | 0.04 | < 2 | 21 | 5 |

With the use of AlEtCl₂, cyclization reactions were observed, caused by the stronger Friedel-Crafts activity of the higher-halogenated organoaluminum compounds. The proportion of trans-1,4-linkages in the polymer has increased considerably.

With the utilization of triethylaluminum in the concentrations customary for this purpose, only very minor conversions were attained. Even by the addition of acids, such as hydrochloric acid, the ratios were not considerably improved.

EXAMPLE 8

The process of Example 1 was repeated, with the modification that other organophosphorus compounds were used. The results of these polymerizations are set forth in Table VIII.

TABLE VIII

| Experiment No. | Triethyl phosphite: Co Molar Ratio | Conversion (%) | RSV (dl/g) | Gel (%) | Microstructure (%) cis-1,4 | Vinyl |
|---|---|---|---|---|---|---|
| 58 | 0.5 | 84 | 2.6 | < 2 | 87 | 6 |
| 59 | 1 | 80.1 | 2.0 | 4 | 83 | 9 |
| 60 | 2 | 87.8 | 0.57 | < 2 | 84 | 10 |
| 61 | 5 | 43.0 | 0.28 | 3 | 40 | 57 |
|    | ETPB*: Co Molar Ratio |  |  |  |  |  |
| 62 | 0.5 | 85.8 | 1.1 | < 2 | 80 | 11 |
| 63 | 1 | 77.4 | 2.2 | < 2 | 89 | 6 |
| 64 | 2 | 71.8 | 0.86 | < 2 | 86 | 8 |
|    | Diphenyl-allyl-phosphite: Co Molar Ratio |  |  |  |  |  |
| 65 | 0.5 | 60.4 | 0.95 | 18 | 85 | 8 |
| 66 | 1 | 81.0 | 0.62 | 3 | 86 | 9 |
| 67 | 2 | 70.0 | 0.25 | < 2 | 74 | 19 |
| 68 | 5 | 53.1 | 0.1 | 2 | 41 | 56 |
| 69 | 7.5 | 27.7 | 0.12 | 3 | 38 | 58 |
| 70 | 0.5 | 95 | 1.1 | 13 | 88 | 5 |
| 71 | 1 | 99 | 0.27 | < 2 | 71 | 21 |
| 72 | 2 | 46.4 | 1.7 | 2 | 81 | 11 |

*ETPB = 1-Ethyl-3,5,8-trioxa-4-phospha-2,2,2-bicyclooctane

EXAMPLE 9

Under otherwise constant experimental conditions (0.75 millimole of Co octoate; 0.2 ml. of water; 1.5 millimole of triphenylphosphite; 1675 ml. of benzene; 250 g. of 1,3-butadiene; 20.0 millimoles of diethylaluminum chloride), the effect of the temperature on the polymerization was examined. The duration of the experiment was 5 hours.

TABLE IX

| Experiment No. | T (°C.) | Conversion (%) | RSV (dl/g) | Gel (%) | Microstructure (%) | |
|---|---|---|---|---|---|---|
| | | | | | cis-1,4 | Vinyl |
| 81 | 0 | 2.3 | 0.18 | 27 | 16 | 32 |
| 82 | 30 | 58.4 | 0.14 | 2 | 46 | 50 |
| 83 | 40 | 64.8 | 0.09 | <2 | 42 | 53 |
| 84 | 50 | 75.6 | 0.09 | <2 | 43 | 53 |
| 85 | 60 | 62.8 | 0.12 | 2 | 59 | 35 |
| 86 | 70 | 62.6 | 0.09 | <2 | 53 | 33 |

EXAMPLE 10

Under otherwise constant experimental conditions (see Example 9), the chronological course of the polymerization was investigated. The polymerization temperature was 50° C.

TABLE X

| Experiment No. | t (min.) | Conversion (%) | RSV (dl/g) | Gel (%) | Microstructure (%) | |
|---|---|---|---|---|---|---|
| | | | | | cis-1,4 | Vinyl |
| 87 | 1 | 9.2 | 0.16 | 40 | 44 | 33 |
| 88 | 2 | 9.4 | 0.10 | 32 | 40 | 42 |
| 89 | 5 | 15.8 | 0.08 | 11 | 39 | 52 |
| 90 | 10 | 29.2 | 0.1 | 2 | 48 | 46 |
| 91 | 15 | 30.3 | 0.06 | 3 | 47 | 47 |
| 92 | 20 | 37.2 | 0.06 | 3 | 47 | 48 |
| 93 | 30 | 45.6 | 0.08 | <2 | 45 | 50 |
| 94 | 35 | 47.2 | 0.08 | 2 | 42 | 53 |
| 95 | 45 | 69.9 | 0.11 | 2 | 46 | 48 |
| 96 | 60 | 66.1 | 0.11 | <2 | 45 | 51 |
| 97 | 120 | 68.3 | 0.11 | <2 | 43 | 54 |
| 98 | 180 | 70.6 | 0.06 | <2 | 46 | 49 |
| 99 | 300 | 75.6 | 0.09 | <2 | 43 | 53 |

EXAMPLE 11

Instead of 1,3-butadiene, isoprene (250 g.) was polymerized as indicated in Example 1. The results are set forth in Table XI.

TABLE XI

| Experiment No. | P:Co Molar Ratio | Conversion (%) | (dl/g) | (%) | Microstructure (%) | | |
|---|---|---|---|---|---|---|---|
| | | | | | 1,2 | 3,4 | 1,4 |
| 100 | 0.5 | 47.2 | 1.1 | 20 | 7 | 32 | 61 |
| 101 | 1 | 70.8 | 0.85 | <2 | 16 | 44 | 60 |
| 102 | 2 | 67.6 | 0.75 | 2 | 11.4 | 41.6 | 47 |
| 103 | 5 | 8.2 | 1.3 | 6 | — | — | — |

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A process for the production of low molecular weight butadiene polymers having a molecular weight distribution of between 1 and 1.5 and whose double bonds are 10–70% vinyl, 30—90% 1,4-cis and 0–10% 1,4-trans, by the polymerization of butadiene, in bulk or in the presence of a solvent, which comprises employing as the catalyst system:
   a. 0.01 to 0.5 millimole per mole of monomer to be catalyzed of one or both of cobalt octoate and cobalt acetylacetonate;
   b. a dialkyl aluminum halide in an amount such that the molar ratio of the cobalt in (a) to the aluminum in (b) is from 1:1 to 1:2,000;
   c. triphenyl phosphite, in a molar ratio to (a) of from 0.3:1 to 10:1; and
   d. an H-acidic compound in a molar ratio to the aluminum in (b) of up to 1.5:1.
2. A process according to claim 1 wherein the H-acidic compound is water.
3. A process according to claim 1 wherein (a) is cobalt octoate.
4. A process according to claim 1 wherein the dialkylaluminum halide is dimethylaluminum chloride, diethylaluminum chloride or diisobutylaluminum chloride.
5. A process according to claim 1 wherein the catalyst system is
   a. 0.01 to 0.5 millimoles per mole of monomer to be polymerized of cobalt octoate;
   b. diethylaluminum chloride, in an amount such that the molar ratio of cobalt in (a) to the aluminum in (b) is from 1:10 to 1:100;
   c. triphenylphosphite in a molar ratio to (a) of from 0.3:1 to 10:1; and
   d. water.
6. A catalyst system for polymerizing conjugated dienes consisting essentially of
   a. one or both of cobalt octoate and cobalt acetylacetonate;
   b. a dialkyl aluminum halide in an amount such that the molar ratio of the cobalt in (a) to the aluminum in (b) is from 1:1 to 1:2,000;
   c. triphenyl phosphite, in a molar ratio to (a) of from 0.3:1 to 10:1, and
   d. an H-acidic compound in a molar ratio to the aluminum in (b) of up to 1.5:1.
7. A catalyst system according to claim 6 wherein the H-acidic compound is water.
8. A catalyst system according to claim 6 wherein (a) is cobalt octoate.
9. A catalyst system according to claim 6 wherein the dialkylaluminum halide is dimethylaluminum chloride, diethylaluminum chloride or diisobutylaluminum chloride.
10. A catalyst system according to claim 6 consisting essentially of
   a. cobalt octoate;
   b. diethylaluminum chloride, in an amount such that the molar ratio of cobalt in (a) to the aluminum in (b) is from 1:10 to 1:100;
   c. triphenylphosphite in a molar ratio to (a) of from 0.3:1 to 10:1; and
   d. water.

* * * * *